(12) United States Patent
Yachi (10) Patent No.: US 9,961,761 B2
(45) Date of Patent: May 1, 2018

(54) RADIATION IMAGING APPARATUS AND IMAGING SYSTEM (71) Applicant: CANON KABUSHIKI KAISHA, Tokyo (JP)

(72) Inventor: Katsuya Yachi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 239 days.

(21) Appl. No.: 15/091,667

(22) Filed: Apr. 6, 2016

(65) Prior Publication Data

US 2016/0302302 A1    Oct. 13, 2016

(30) Foreign Application Priority Data

Apr. 13, 2015   (JP) ................. 2015-082064

(51) Int. Cl.
*H01J 31/49*  (2006.01)
*H05K 1/02*   (2006.01)
*H05K 1/14*   (2006.01)
*A61B 6/00*   (2006.01)

(52) U.S. Cl.
CPC ......... *H05K 1/0216* (2013.01); *A61B 6/4266* (2013.01); *A61B 6/5258* (2013.01); *H05K 1/141* (2013.01); *H05K 2201/0707* (2013.01); *H05K 2201/10151* (2013.01); *H05K 2201/10606* (2013.01)

(58) Field of Classification Search
CPC ...... H01K 1/0216; A61B 6/54; A61B 6/4266; A61B 6/5258; H05K 1/0216; H05K 1/141; H05K 2201/10151; H05K 2201/10606; H05K 2201/0707
See application file for complete search history.

(56) References Cited

U.S. PATENT DOCUMENTS

2012/0074331 A1*  3/2012  Koyanagi .............. G03B 42/04
                                                              250/394
2012/0228499 A1*  9/2012  Koyanagi .............. G03B 42/04
                                                              250/336.1

FOREIGN PATENT DOCUMENTS

JP        2002-214729       7/2002

* cited by examiner

*Primary Examiner* — Courtney Thomas
(74) *Attorney, Agent, or Firm* — Fitzpatrick Cella Harper and Scinto

(57) ABSTRACT

A radiation imaging apparatus, comprising a sensor panel in which a plurality of sensors configured to detect radiation are arrayed, a first circuit board that is arranged on the sensor panel and includes a circuit configured to read out a signal from each sensor, and a second circuit board that is arranged on the first circuit board and includes a circuit configured to read out a signal from each sensor, and whose radiant noise generation amount at a driving time of the circuit is larger than a radiant noise generation amount at a driving time of the circuit of the first circuit board, wherein the first circuit board is arranged between the sensor panel and the second circuit board.

20 Claims, 7 Drawing Sheets

RADIATION IMAGING APPARATUS AND IMAGING SYSTEM

BACKGROUND OF THE INVENTION

Field of the Invention

The present invention relates to a radiation imaging apparatus and an imaging system.

Description of the Related Art

A radiation imaging apparatus includes, for example, a sensor panel in which a plurality of sensors are arrayed, a plurality of circuit boards for reading out signals from the sensors of the sensor panel, and a housing which includes these parts. The plurality of circuit boards include, for example, an analog circuit board, a digital circuit board, and a power supply circuit board. The analog circuit board includes, for example, an analog circuit that performs signal processing (for example, signal amplification processing, A/D conversion, or the like) on each signal received from the sensor panel. The digital circuit board includes, for example, a digital circuit that performs signal processing (for example, correction processing or the like) on each A/D converted signal. The power supply circuit board includes, for example, a power supply circuit that generates voltages to be supplied to other circuit boards such as the analog circuit board and the like. The power supply circuit forms, for example, a switching power supply or the like.

In general, the radiant noise generation amount is different for each above-described circuit board. In the above-described example, the radiant noise generation amount is comparatively large in the power supply circuit board. The sensor signal output from each sensor is easily influenced by radiant noise and its signal value changes due to the radiant noise.

Japanese Patent Laid-Open No. 2002-214729 discloses a structure in which a sensor panel and a power supply circuit board are arranged side by side in the horizontal direction (a direction parallel to a radiation detection face of the sensor panel) in a housing and the sensor panel and the power supply circuit are isolated by a metal partition. This structure reduces the influence of noise from the power supply circuit board to the sensor panel. However, this structure increases the size of the housing in the horizontal direction.

SUMMARY OF THE INVENTION

The present invention provides a technique advantageous in reducing the influence of radiant noise from a circuit board on a sensor panel while suppressing an increase in the size of a radiation imaging apparatus.

One of the aspects of the present invention provides a radiation imaging apparatus comprising: a sensor panel in which a plurality of sensors configured to detect radiation are arrayed; a first circuit board that is arranged on the sensor panel and includes a circuit configured to read out a signal from each sensor; and a second circuit board that is arranged on the first circuit board and includes a circuit configured to read out a signal from each sensor, and whose radiant noise generation amount at a driving time of the circuit is larger than a radiant noise generation amount at a driving time of the circuit of the first circuit board, wherein the first circuit board is arranged between the sensor panel and the second circuit board.

Further features of the present invention will become apparent from the following description of exemplary embodiments with reference to the attached drawings.

DESCRIPTION OF THE EMBODIMENTS

First Embodiment

Figure 1A:
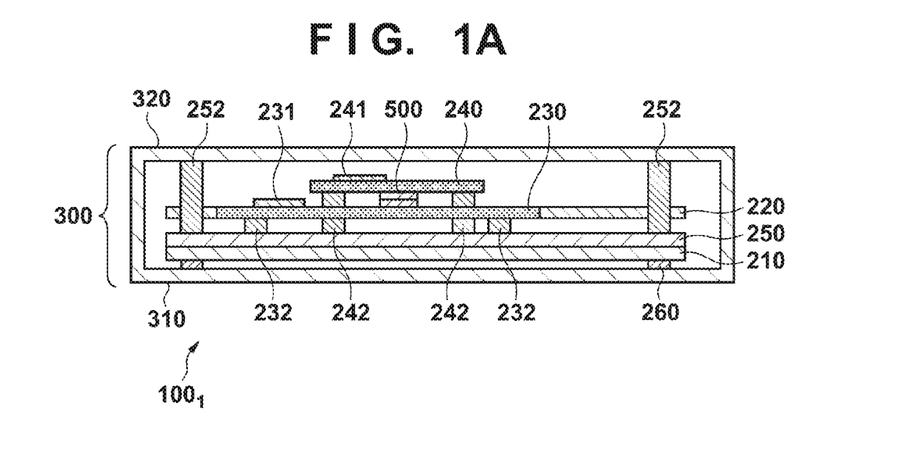
FIGS. 1A, 1B, and 1C are views for explaining an example of the structure of a radiation imaging apparatus.
Figure 1B:
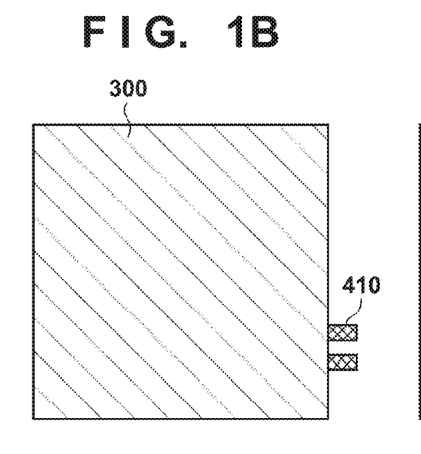
Figure 1C:
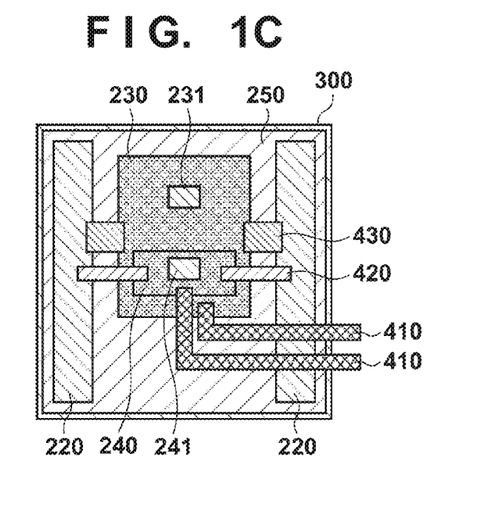

The first embodiment will be described with reference to FIGS. 1A to 1C and 2. FIGS. 1A to 1C are schematic views for explaining an example of the structure of a radiation imaging apparatus $100_1$. FIG. 1A shows the sectional structure of the radiation imaging apparatus $100_1$. The radiation imaging apparatus $100_1$ includes, for example, a sensor panel 210, analog circuit boards 220, a digital circuit board 230, a power supply circuit board 240, a support plate 250, and a housing 300 which includes these components.

The sensor panel 210 has, for example, a scintillator and a plurality of sensors arrayed on a substrate such as a glass substrate. The sensor is made of, for example, amorphous silicon and can include a PIN sensor, a MIS sensor or the like. The sensor panel 210 detects radiation by converting the radiation (typically X-rays) into light via the scintillator and photoelectrically converting the light via the sensor. In other embodiments, the sensor panel 210 can be formed to directly convert radiation into electrical signals.

One or more IC chips for implementing corresponding functions are arranged on each of the circuit boards 220, 230, and 240. The analog circuit boards 220 each include an analog circuit and perform amplification processing on analog signals from the sensor panel 210 and signal processing such as analog/digital conversion or the like. The digital circuit board 230 includes a digital circuit and performs, via the digital circuit, signal processing such as correction processing on the A/D converted signal and generates image data. In addition, although details will be described later, a power supply circuit 231 which forms a switching power supply is arranged on the digital circuit board 230, and a power supply circuit 241 which forms a switching power supply is arranged on the power supply circuit board 240.

The support plate 250 supports the sensor panel 210, the analog circuit boards 220, the digital circuit board 230, and the power supply circuit board 240. In other words, the sensor panel 210, the analog circuit boards 220, the digital circuit board 230, and the power supply circuit board 240 are fixed to the supporting plate 250. For example, the sensor panel 210 is fixed to the side of one face (the lower face in FIG. 1A) of the support plate 250 by an adhesive. The digital circuit board 230 is fixed to the side of the other face (the upper face in FIG. 1A) of the support plate 250 by columns 232. The power supply circuit board 240 is also fixed to the side of the other face of the support plate 250 by columns 242. In a similar manner, the analog circuit boards 220 are fixed to the side of the other face of the support plate 250 by columns (not shown).

The housing 300 includes, for example, a first member 310 and a second member 320. The member 310 is, for example, a plate-shaped plate member made of carbon fiber reinforced plastic and arranged on the radiation incident side (irradiation side). The sensor panel 210 is arranged between the member 310 and the support plate 250. Buffer members 260 can be arranged between the sensor panel 210 and the member 310. A material which has a larger degree of shrinkage than the other surrounding members can be used for the buffer members 260. Note that a metal member (not shown) for shielding radiation can be arranged between the sensor panel 210 and the support plate 250.

The member 320 is made of a metal such as steel or aluminum and arranged on the opposite side (reverse face side) of the member 310. The support plate 250 which supports the sensor panel 210, the analog circuit boards 220, the digital circuit board 230, and the power supply circuit board 240 is fixed to the member 320 by columns 252. The analog circuit boards 220, the digital circuit board 230, and the power supply circuit board 240 are arranged between the member 320 and the support plate 250. The power supply circuit 240 is arranged at a position far from the sensor panel 210 than the analog circuit boards 220 and the digital circuit board 230. Although the analog circuit boards 220 and the digital circuit board 230 are arranged at positions having the same distance from the sensor panel 210 in FIG. 1A, they can be arranged at different distances from the sensor panel 210.

FIG. 1B shows the structure of the radiation imaging apparatus $100_1$ viewed from the side of the member 320, and FIG. 1C shows the internal structure of the housing 300 according to FIG. 1B. In this example, two analog circuit boards 220 are arranged, in a planar view, in the peripheral region (along one side and the other opposite side) of the support plate 250. Note that in this specification, "planar view" indicates a planar view with respect to the radiation detection face of the sensor panel 210 (to be referred to in the same manner hereinafter).

The digital circuit board 230 and the power supply circuit board 240 are arranged in the central region of the support plate 250, in between the above-mentioned two analog circuit boards 220 in a planar view. The digital circuit board 230 and the power supply circuit board 240 are also arranged to overlap each other in a planar view. From another viewpoint, the power supply circuit board 240 is arranged right above the digital circuit board 230 in FIG. 1A.

The digital circuit board 230 and the power supply circuit board 240 are connected to the outside by cables 410. The cables 410 are, for example, wiring line groups (for example, flexible flat cables) including a wiring line for receiving external power, a wiring line for exchanging signals from/to the outside, and the like. For example, other than the digital circuit, the digital circuit board 230 includes a power supply circuit 231 which forms the switching power supply. Based on the external power received via the corresponding cable 410, the power supply circuit 231 generates a voltage which is to be supplied to the digital circuit of the digital circuit board 230. In addition, for example, the power supply circuit board 240 includes the power supply circuit 241 which forms the switching power supply. Based on the external power received from the corresponding cable 410, the power supply circuit 241 generates a voltage which is to be supplied to the analog circuit of each analog circuit board 220. Furthermore, the power supply circuit 241 can also generate a voltage which is to be supplied to the sensor panel 210.

The analog circuit boards 220 and the power supply circuit board 240 are connected by cables 420 (for example, flexible flat cables), and the analog circuit boards 220 receive voltages from the power supply circuit board 240 via the cables 420. The analog circuit boards 220 and the digital circuit board 230 are connected by cables 430 (for example, flexible flat cables), and the digital circuit board 230 receives signals from the analog circuit boards 220 via the cables 430. The digital circuit board 230 and the power supply circuit board 240 are connected by connectors 500 and can control each other or one can control the other. The digital circuit board 230 also outputs, to the outside via the corresponding cable 410, image data generated based on the signals received from the analog circuit boards 220 (that is, image data based on signals read out from the sensor panel 210).

In general, the current supply amount to the digital circuit (or power necessary for driving the digital circuit) is comparatively small whereas the current supply amount to the analog circuit (or power necessary for driving the analog circuit) is comparatively large. Hence, in this example, the radiant noise generation amount in the power supply circuit 231 which generates the voltage to be supplied to the digital circuit is comparatively small whereas the radiant noise generation amount in the power supply circuit 241 which generates the voltage to be supplied to the analog circuits is comparatively large.

Therefore, in this embodiment, in contrast to the power supply circuit 231 which is provided on the digital circuit board 230, the power supply circuit 241 is provided on another circuit board (the power supply circuit board 240 in this example). In addition, the digital circuit board 230 is arranged between the sensor panel 210 and the power supply circuit board 240 so that the digital circuit board 230 and the power supply circuit board 240 will overlap each other in a planar view. The digital circuit board 230 can accordingly act as a noise shield that blocks radiant noise from the power supply circuit board 240 to the sensor panel 210.

The area of the digital circuit board 230 is preferably larger than that of the power supply circuit board 240 in a planar view. From another viewpoint, the edge of the digital circuit board 230 is preferably positioned outside the edge of the power supply circuit board 240. This allows the digital circuit board 230 to appropriately block radiant noise from the power supply circuit board 240 to the sensor panel 210.

Metal members such as the wiring line pattern and the like belonging to the digital circuit board 230 can be conducive to block radiant noise. Therefore, for example, the wiring line pattern for supplying a constant voltage (for example, a ground voltage) to the digital circuit is preferably provided at a high density. The wiring line pattern or at least a part of the wiring line pattern can have, for example, a substantially plate-shaped form. The wiring line pattern or at least a part of the wiring line pattern can also have, for example, a substantially grid-shaped or strip-shaped form. These types of structures will improve the resistance to noise of the digital circuit itself and allow the digital circuit board 230 to appropriately act as a noise shield.

Figure 2:
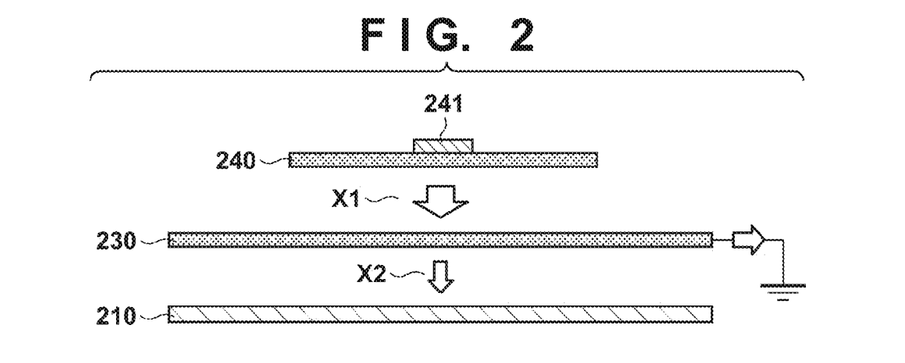
FIG. 2 is a view for explaining the influence of radiant noise between a sensor panel and circuit boards.

FIG. 2 is a view for explaining the influence of radiant noise between the sensor panel 210 and the circuit boards 230, and 240. As shown in FIG. 2, at least a part of radiant noise X1 generated in the power supply circuit 241 of the power supply circuit board 240 is shielded (or absorbed) by the metal members such as the wiring line pattern and the like belonging to the digital circuit board 230. Accordingly, radiant noise X2 that reaches the sensor panel 210 can be reduced.

The radiation imaging apparatus $100_1$ has a so-called vertically stacked circuit board structure in which the digital circuit board 230 and the power supply circuit board 240 are arranged in the vertical direction. Therefore, according to this structure, the influence of radiant noise to the sensor panel 210 can be reduced and size increase in the horizontal direction of the radiation imaging apparatus $100_1$ can be suppressed.

According to the first embodiment, the influence of radiant noise from each circuit board (particularly the influence of radiant noise from the power supply circuit board 240) to the sensor panel 210 can be reduced while suppressing the size increase of the radiation imaging apparatus $100_1$.

Second Embodiment

Figure 3A:
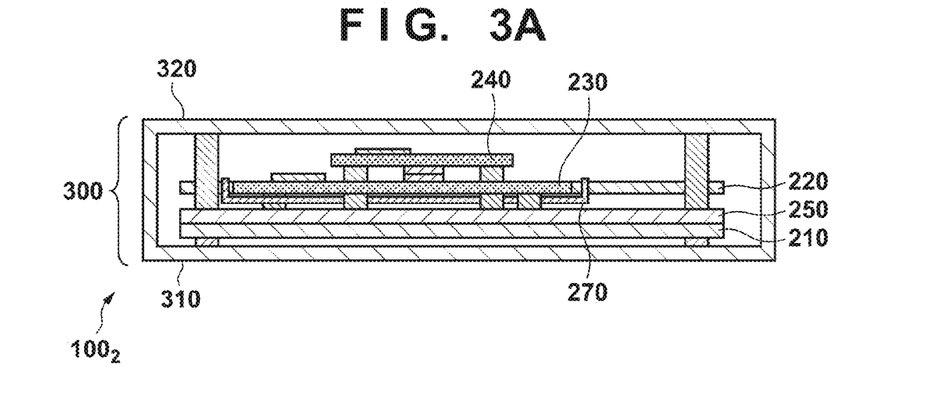
FIGS. 3A, 3B, and 3C are views for explaining an example of the structure of a radiation imaging apparatus.
Figure 3B:
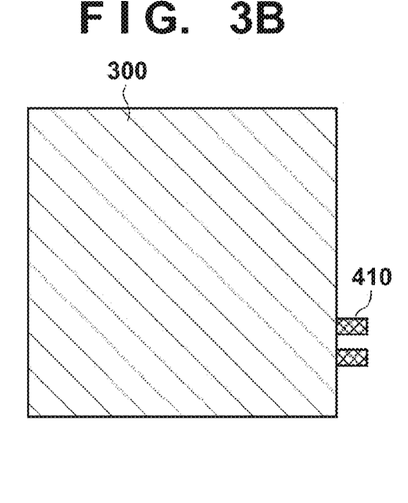
Figure 3C:
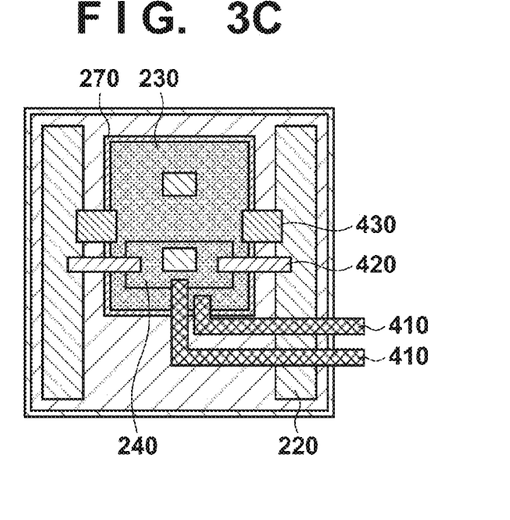

A radiation imaging apparatus $100_2$ according to the second embodiment of the present invention will be described with reference to FIGS. 3A to 3C. FIGS. 3A to 3C show an example of the structure of the radiation imaging apparatus $100_2$ in the same manner as that in the aforementioned first embodiment (FIGS. 1A to 1C). The second embodiment mainly differs from the first embodiment in that a shield member 270 for blocking radiant noise is arranged between a digital circuit board 230 and a support plate 250. According to the second embodiment, in addition to preventing the radiant noise generated in the digital circuit board 230 from reaching a sensor panel 210, radiant noise generated from a power supply circuit board 240 and attenuated by the digital circuit board 230 can be prevented from reaching the sensor panel 210.

The shield member 270 preferably has, in a planar view, an area larger than the area of the digital circuit board 230 and is arranged so that the shield member 270 and the digital circuit board 230 overlap each other. In other words, the outer edge of the shield member 270 is preferably positioned outside the edge of the digital circuit board 230. In this case, the shield member 270 can also include portions arranged to fully or partially cover the side faces of the digital circuit board 230. In other words, the shield member 270 can be arranged so that each part of the shield member 270 and the corresponding side face or its part of the digital circuit board 230 are facing each other.

According to the second embodiment, the influence of radiant noise to the sensor panel 210 can be further reduced.

Third Embodiment

Figure 4A:
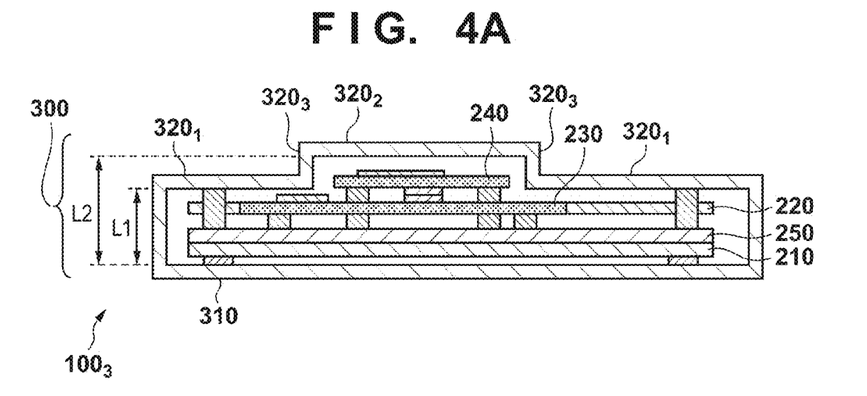
FIGS. 4A, 4B, and 4C are views for explaining an example of the structure of a radiation imaging apparatus.
Figure 4B:
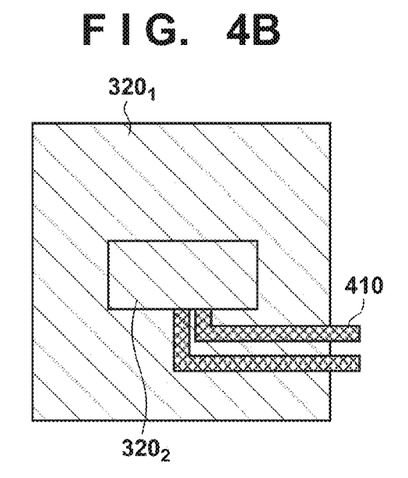
Figure 4C:
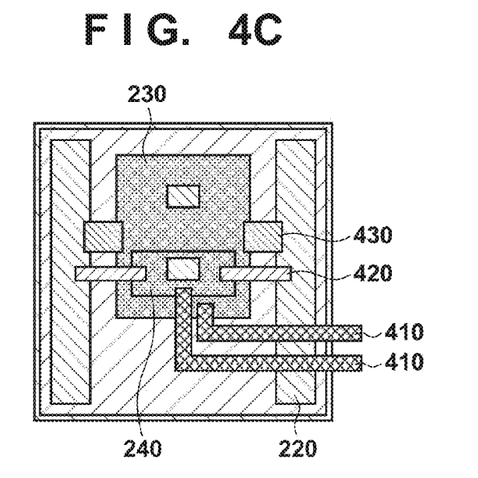

A radiation imaging apparatus $100_3$ according to the third embodiment will be described with reference to FIGS. 4A to 4C. FIGS. 4A to 4C show an example of the structure of the radiation imaging apparatus $100_3$ in the same manner as that in the aforementioned first embodiment (FIGS. 1A to 1C). The third embodiment mainly differs from the first embodiment in that a member 320 of a housing 300 includes portions $320_1$ to $320_3$ that form a convex shape.

Each portion $320_1$ is a first portion, out of the member 320, whose distance from a member 310 is a distance L1. The portion $320_2$ is a second portion, out of the member 320, whose distance from the member 310 is a distance L2 longer than the distance L1 and forms a portion protruding toward the outer side of the housing 300 with respect to the portions $320_1$. Each portion $320_3$ is a third portion which connects the portion $320_1$ and the portion $320_2$ and forms a side face portion of the above-described protruding portion. Note that a support plate 250 can be fixed to the portions $320_1$ of the member 320 out of the housing 300.

A digital circuit board 230 that includes a power supply circuit 231 having a comparatively small radiant noise generation amount is arranged between the support plate 250 and the portions $320_1$. In contrast, a power supply circuit board 240 that includes a power supply circuit 241 having a comparatively large radiant noise generation amount is arranged between the support plate 250 and the portion $320_2$ so that the distance from a sensor panel 210 will be longer than the distance between the digital circuit board 230 and the sensor panel 210. For example, the power supply circuit board 240 is arranged near the portion $320_2$ so that the upper face of the power supply circuit board 240 is at a position higher than the lower face of each portion $320_1$ and at least a part of each side face of the power supply circuit board 240 and a part of the corresponding surface of each portion $320_3$ face each other. The distance between the power supply circuit board 240 and the member 310 can be longer than the distance L1 and shorter than the distance L2.

According to this arrangement, the horizontal direction components out of the radiant noise from the power supply circuit board 240 are shielded by the portion $320_3$ and can be prevented from passing each side face and its vicinity of the digital circuit board 230 and reaching the sensor panel 210. Therefore, according to the third embodiment, the influence of radiant noise to the sensor panel 210 can be further reduced.

Figure 5:
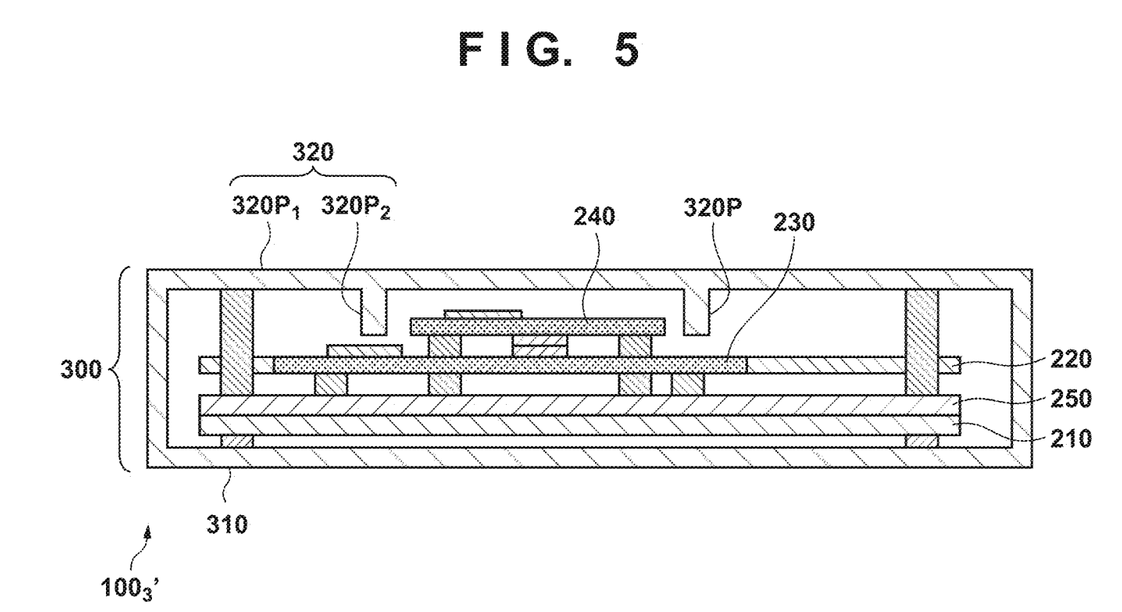
FIG. 5 is a view for explaining another example of the structure of the radiation imaging apparatus.

FIG. 5 shows an example of the structure of a radiation imaging apparatus $100_3'$ as another example of the third embodiment in the same manner as that in FIG. 4A. The example of this structure mainly differs from that in the example of FIGS. 4A to 4C in that the member 320 of the housing 300 includes a plate-shaped portion $320P_1$ and portions $320P_2$ protruding from the portion $320P_1$ toward the inside of the housing 300. According to the example of this structure, at least a part of each side face of the power supply circuit board 240 and a part of the corresponding surface of each portion $320P_2$ face each other. Therefore, the example of this structure can also shield, by the portions $320P_2$, the horizontal direction components out of the radiant noise from the power supply circuit 240 and prevent the components from passing each side face and its vicinity of the digital circuit board 230 and reaching the sensor panel 210.

Others

Several preferred embodiments have been described above, but the present invention is not limited to them. The embodiments may be partially changed without departing from the scope or spirit of the invention.

For example, the embodiments exemplified a mode in which the respective radiation imaging apparatuses $100_1$ to $100_3$ (to be simply referred to as "radiation imaging apparatus 100" here in after) included two analog circuit boards 220. In this example, one of the two analog circuit boards 220 performs signal processing on some of the signals read out from the sensor panel 210 and the other of the two analog circuit boards 220 performs signal processing on some of the other signals read out from the sensor panel 210. However, the radiation imaging apparatus 100 can include one analog circuit board 220 and perform signal processing of all the signals read out from the sensor panel 210 by the one analog circuit board 220.

Figure 6A:
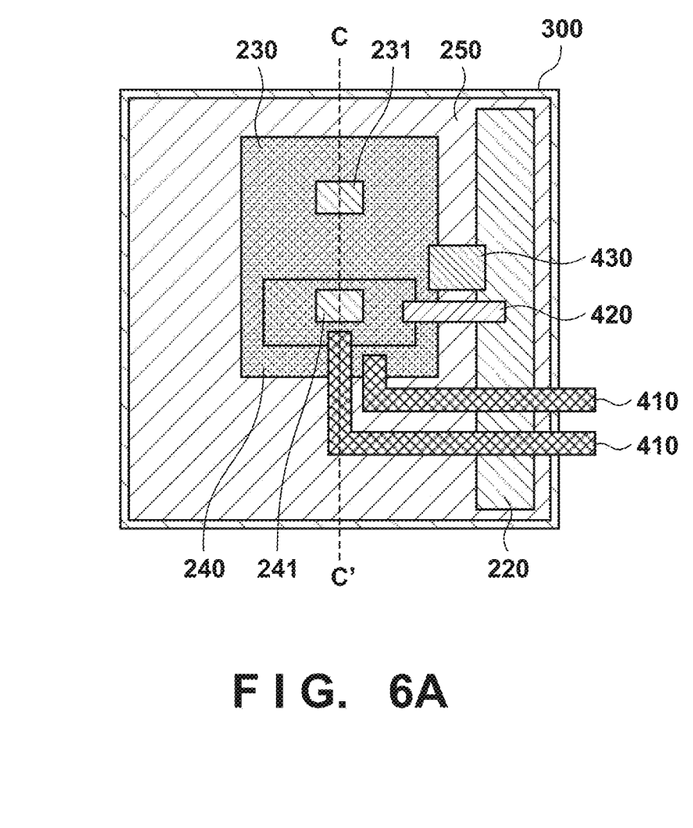
FIGS. 6A and 6B are views for explaining an example of the structure of a radiation imaging apparatus.
Figure 6B:
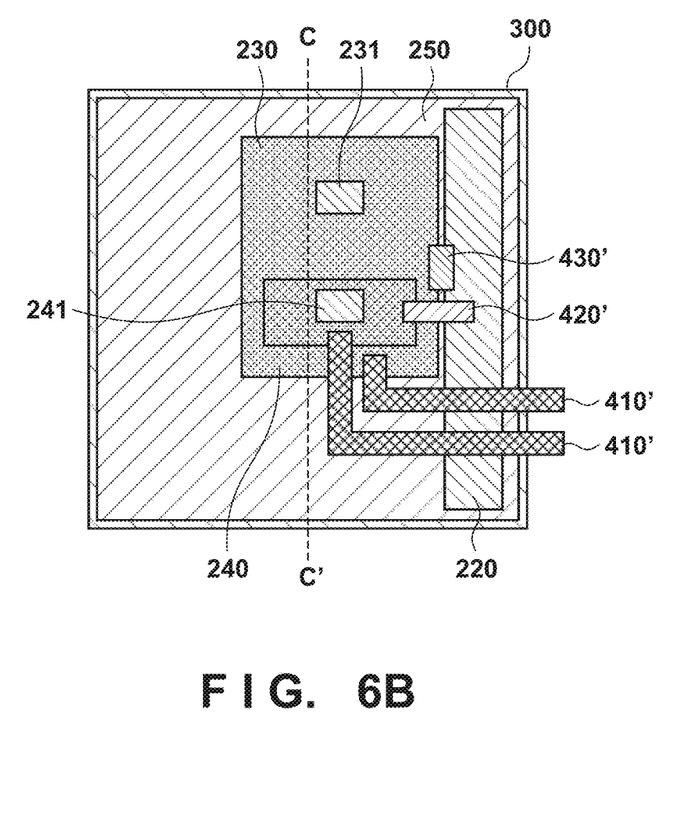

In this example, as shown in FIG. 6A, the digital circuit board 230 and the power supply circuit board 240 can be arranged in the central region of the support plate 250 (so that the circuit boards will be bilaterally symmetrical with respect to a center line C-C' in FIG. 6A as the reference line) in planar view, in the same manner as the aforementioned embodiments. However, as shown in FIG. 6B, the digital circuit board 230 and the power supply circuit board 240 can be arranged near the one analog circuit board 220 (so that the circuit boards will shift to the side of the one analog circuit board 220 with respect to the center line C-C' of in FIG. 6B). According to the example of FIG. 6B, the lengths of cables 410' to 430' can be shorter than the lengths of the cables 410 to 430 in the example of FIG. 6A. This can reduce the impedance components in wiring lines included in the cables 410' to 430'.

Other components such as the number, shape and arrangement of members or parts (for example, circuit boards, heat conductive members, adiabatic members, and the like) to be included in the housing 300 can be appropriately changed without departing from the scope of the present invention. Note that this specification described the positional relationship of some of the exemplified plurality of members for the sake of clarity of the structure of the radiation imaging apparatus 100. However, it goes without saying that the positions of the members are relatively defined and can be defined in relation to other members without departing from the scope of the present invention.

Radiation Imaging System

Figure 7:
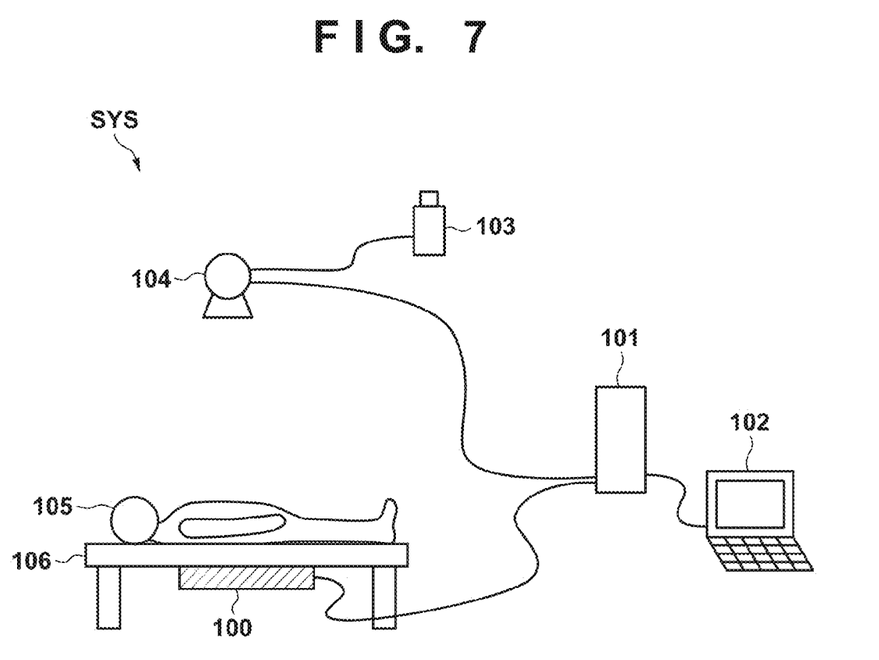
FIG. 7 is a view for explaining an example of the arrangement of an imaging system that uses a radiation imaging apparatus.

FIG. 7 shows an example of the arrangement of an imaging system SYS in which the radiation imaging apparatus 100 has been applied. The imaging system SYS includes, for example, the radiation imaging apparatus 100, a processor 101, a terminal 102, an exposure switch 103, and a radiation source 104. The radiation imaging apparatus 100 is attached to, for example, a bed 106 on which an object 105 such as a patient is to be laid. The radiation imaging apparatus 100 receives the radiation emitted from the radiation source 104 and passed through the patient 105 and outputs, to the processor 101, image data in accordance with the radiation. The processor 101 causes the display of the terminal 102 to display a radiation image according to the image data from the radiation imaging apparatus 100. The processor 101 can perform predetermined data processing on the image data from the radiation imaging apparatus 100.

In addition, the processor 101 can function as a controller for controlling the entire system and can control each unit so that radiation imaging is appropriately performed in accordance with imaging conditions or the like input to the terminal 102 by a user. The processor 101 can also control the radiation source 104 by determining whether the radiation imaging apparatus 100 is in a state where radiation imaging can be started. In this case, the radiation source 104 generates radiation when the user presses the exposure switch 103 in a state where the radiation imaging apparatus 100 can start radiation imaging.

Figure 8:
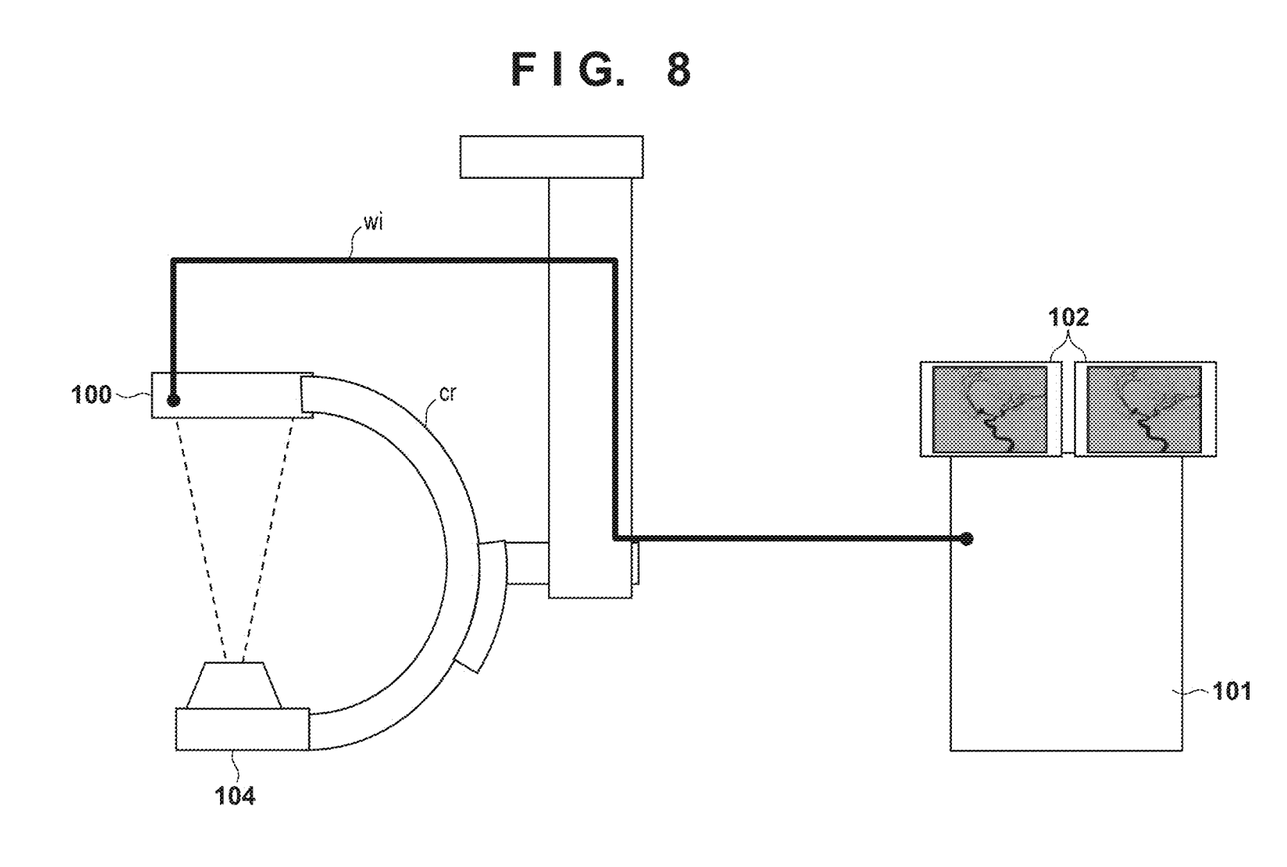
FIG. 8 is a view for explaining another example of the arrangement of the imaging system that uses the radiation imaging apparatus.

FIG. 8 shows a C-arm type radioscopic diagnosis apparatus (to be referred to as "C-arm apparatus" hereinafter) as another example of the arrangement of the imaging system SYS. In the C-arm apparatus, the radiation imaging apparatus 100 and the radiation source 104 are fixed to the two ends of a C-arm cr. The C-arm apparatus performs radiation imaging (3D imaging) while changing an irradiation angle by rotating the arm cr. The image data obtained by the radiation imaging apparatus 100 is output to the processor 101 via, for example, a cable wi. The processor 101 forms a three-dimensional radiation image based on the image data and causes the display of the terminal 102 to display the image.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-082064, filed Apr. 13, 2015, which is hereby incorporated by reference herein in its entirety.

What is claimed is:

1. A radiation imaging apparatus comprising:
   a sensor panel in which a plurality of sensors configured to detect radiation are arrayed;
   a first circuit board that is arranged on the sensor panel and includes a circuit configured to read out a signal from each sensor; and
   a second circuit board that is arranged on the first circuit board and includes a circuit configured to read out a signal from each sensor, and whose radiant noise generation amount at a driving time of the circuit is larger than a radiant noise generation amount at a driving time of the circuit of the first circuit board,
   wherein the first circuit board is arranged between the sensor panel and the second circuit board.

2. The apparatus according to claim 1, wherein the first circuit board acts as a noise shield configured to block radiant noise from the second circuit board to the sensor panel.

3. The apparatus according to claim 1, wherein in a planar view with respect to a radiation detection face of the sensor panel, the first circuit board has an area larger than that of the second circuit board, and the first circuit board and the second circuit board are positioned to overlap each other.

4. The apparatus according to claim 1, further comprising:
   a shield member that is arranged between the sensor panel and the first circuit board and configured to block radiant noise from the first circuit board to the sensor panel.

5. The apparatus according to claim 4, wherein the shield member includes a portion formed to cover a corresponding side face of the first circuit board.

6. The apparatus according to claim 1, wherein the first circuit board further has a wiring line pattern for supplying a constant voltage to the circuit belonging to the first circuit board, and
   at least a part of the wiring line pattern has, in a planar view with respect to a radiation detection face of the sensor panel, one of a plate-shaped form, a grid-shaped form, and a strip-shaped form.

7. The apparatus according to claim 1, further comprising:
   a housing including the sensor panel, the first circuit board, and the second circuit board,
   wherein the housing includes
   a plate-shaped first member positioned on the sensor panel side, and
   a second member that is positioned on the opposite side of the first member and includes a first portion whose distance from the first member is a first distance and a second portion whose distance from the first member is a second distance longer than the first distance, and the first circuit board is arranged, between the sensor panel and the second member, at a position whose distance from the first member is shorter than the first distance, and the second circuit board is arranged between the sensor panel and the second portion of the second member so that the distance from the sensor panel is longer than the distance between the first circuit board and the sensor panel.

8. The apparatus according to claim 7, wherein the second member further includes a third portion that connects the first portion and the second portion, and the third portion is so configured that radiant noise generated in the second circuit is prevented from passing a side face and a vicinity of the first circuit board and reaching the sensor panel.

9. The apparatus according to claim 8, wherein at least a part of a surface of the third portion faces a corresponding side face of the second circuit board.

10. The apparatus according to claim 1, further comprising:

a housing including the sensor panel, the first circuit board, and the second circuit board, wherein the housing includes a plate-shaped first member facing the sensor panel, and a second member that is positioned on the opposite side of the first member and includes a plate-shaped first portion and a second portion protruding from the first portion to a vicinity of a side face of the second circuit board.

11. The apparatus according to claim 8, wherein the second portion is so configured that radiant noise generated in the second circuit board is prevented from passing a side face and a vicinity of the first circuit board and reaching the sensor panel.

12. The apparatus according to claim 11, wherein at least a part of a surface of the second portion faces a corresponding side face of the second circuit board.

13. The apparatus according to claim 7, further comprising:

a support plate that is included in the housing and arranged between the sensor panel and the first circuit board and configured to support the sensor panel, the first circuit board, and the second circuit board.

14. The apparatus according to claim 1, further comprising:

a third circuit board in which an analog circuit for processing an analog signal read out from each sensor is arranged, wherein the circuit arranged on the first circuit board is a digital circuit for processing a signal processed and A/D converted by the analog circuit, and the circuit arranged on the second circuit board is a power supply circuit configured to generate a voltage to be supplied to the analog circuit.

15. The apparatus according to claim 14, wherein the power supply circuit configures a switching power supply.

16. The apparatus according to claim 14, wherein the first circuit board further includes another power supply circuit that is different from the power supply circuit and configured to generate a voltage to be supplied to the digital circuit.

17. The apparatus according to claim 16, wherein the other power supply circuit configures a switching power supply.

18. The apparatus according to claim 14, further comprising:

a support plate arranged between the sensor panel and the first circuit board and configured to support the sensor panel, the first circuit board, and the second circuit board, wherein in a planar view with respect to a radiation detection face of the sensor panel, the first circuit board and the second circuit board are arranged to overlap a central region of the support plate, and the third circuit board is arranged to overlap a peripheral region of the central region.

19. The apparatus according to claim 14, further comprising:

a fourth circuit board in which an analog circuit for processing an analog signal read out from each sensor, wherein the first circuit board and the second circuit board are arranged, in a planar view with respect to a radiation detection face of the sensor panel, between the third circuit board and the fourth circuit board.

20. An imaging system comprising:

a radiation imaging apparatus; and a processor configured to generate a radiation image based on a signal from the radiation imaging apparatus, wherein the apparatus comprises:

a sensor panel in which a plurality of sensors configured to detect radiation are arrayed;

a first circuit board that is arranged on the sensor panel and includes a circuit configured to read out a signal from each sensor; and a second circuit board that is arranged on the first circuit board and includes a circuit configured to read out a signal from each sensor, and whose radiant noise generation amount at a driving time of the circuit is larger than a radiant noise generation amount at a driving time of the circuit of the first circuit board, and wherein the first circuit board is arranged between the sensor panel and the second circuit board.

* * * * *